US009925365B1

(12) United States Patent
Ryan et al.

(10) Patent No.: US 9,925,365 B1
(45) Date of Patent: Mar. 27, 2018

(54) NEEDLELESS IV INJECTION PORT

(71) Applicant: RyMed Technologies, LLC, Austin, TX (US)

(72) Inventors: Dana Wm. Ryan, Mt. Juliet, TN (US); Anthony E. Ryherd, Austin, TX (US); James M. Kaiser, Austin, TX (US)

(73) Assignee: RyMed Technologies, LLC, Austin, TX (US)

( * ) Notice: Subject to any disclaimer, the term of this patent is extended or adjusted under 35 U.S.C. 154(b) by 0 days.

(21) Appl. No.: 15/628,990

(22) Filed: Jun. 21, 2017

(51) Int. Cl.
*A61M 39/26* (2006.01)
*A61M 39/10* (2006.01)
*A61M 5/168* (2006.01)

(52) U.S. Cl.
CPC ........ *A61M 39/26* (2013.01); *A61M 5/16813* (2013.01); *A61M 39/1011* (2013.01); *A61M 2039/267* (2013.01); *A61M 2202/04* (2013.01)

(58) Field of Classification Search
CPC .......... A61M 39/1011; A61M 5/16813; A61M 2039/1072; A61M 2039/262; A61M 2039/267; A61M 39/26; A61M 39/10; A61M 2039/261; A61M 2039/263
See application file for complete search history.

(56) References Cited

U.S. PATENT DOCUMENTS

| 5,700,248 A | 12/1997 | Lopez |
|---|---|---|
| 5,788,215 A | 8/1998 | Ryan |
| 5,833,213 A | 11/1998 | Ryan |
| 5,928,204 A * | 7/1999 | Lopez ..................... A61M 5/14 604/249 |
| 5,954,313 A | 9/1999 | Ryan |
| 6,113,068 A | 9/2000 | Ryan |
| 6,299,131 B1 | 10/2001 | Ryan |
| 6,994,315 B2 | 2/2006 | Ryan et al. |
| 7,530,546 B2 | 5/2009 | Ryan et al. |
| 7,670,322 B2 | 3/2010 | Fangrow, Jr. |
| 7,713,249 B2 | 5/2010 | Lopez |
| 7,717,885 B2 | 5/2010 | Lopez |
| 8,096,525 B2 | 1/2012 | Ryan et al. |
| 8,105,314 B2 | 1/2012 | Fangrow, Jr. |

(Continued)

FOREIGN PATENT DOCUMENTS

WO    9311828 A1    6/1993

OTHER PUBLICATIONS

"InVision-Plus Clear—RyMed Technologies, LLC" website printout (2 pages) (undated but admitted to be prior art).

*Primary Examiner* — Theodore Stigell
(74) *Attorney, Agent, or Firm* — Lucian Wayne Beavers; Patterson Intellectual Property Law, PC

(57) ABSTRACT

A needleless injection port assembly includes first and second body parts and a resilient barrier received within the body. A cannula attached to the first body part is received within an internal cavity of the resilient barrier. The resilient barrier is moveable between a less axially compressed first position in which fluid flow through the injection port assembly is prevented and a more axially compressed second position in which fluid flow through the assembly is allowed. An interference fit is provided between the resilient barrier and the cannula to seal against fluid flow through the cannula when the resilient barrier is in the first position. The cannula has an internal fluid passageway with a non-circular cross section providing increased fluid flow.

25 Claims, 10 Drawing Sheets

(56) References Cited

U.S. PATENT DOCUMENTS

| | | |
|---|---|---|
| 8,152,790 B2 | 4/2012 | Lopez et al. |
| 8,409,164 B2 | 4/2013 | Fangrow |
| 8,454,579 B2 | 6/2013 | Fangrow, Jr. |
| 8,679,090 B2 | 3/2014 | Anderson et al. |
| 8,758,306 B2 * | 6/2014 | Lopez ................. A61M 39/10 604/247 |
| 2003/0199835 A1 | 10/2003 | Leinsing et al. |
| 2007/0007478 A1 | 1/2007 | Leinsing et al. |
| 2010/0249723 A1 | 9/2010 | Fangrow, Jr. |
| 2011/0282302 A1 | 11/2011 | Lopez et al. |
| 2012/0109077 A1 | 5/2012 | Ryan |
| 2015/0011963 A1 | 1/2015 | Fangrow |
| 2016/0001056 A1 | 1/2016 | Nelson et al. |
| 2016/0129235 A1 * | 5/2016 | Ryan ................. A61M 39/1011 604/244 |

* cited by examiner

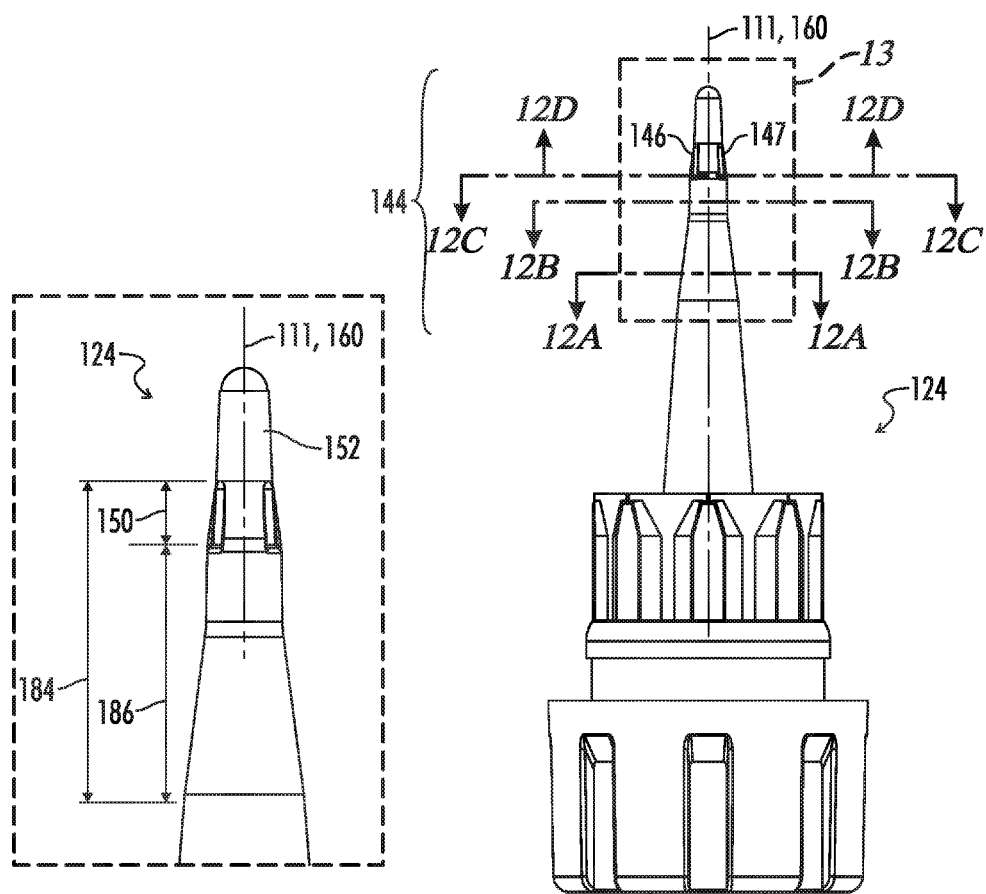
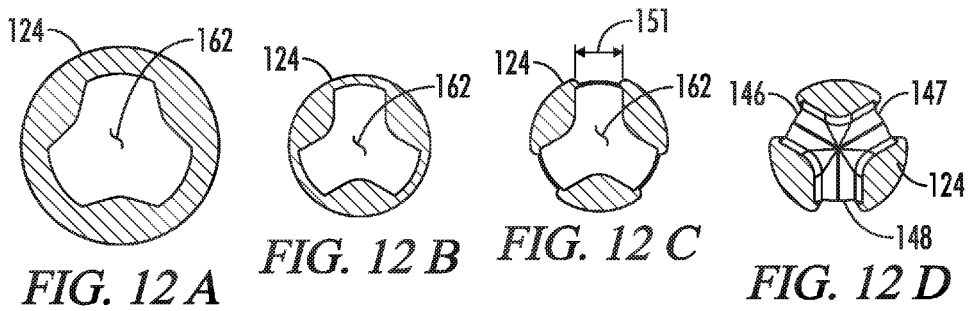
FIG. 13
FIG. 12
FIG. 12 A
FIG. 12 B
FIG. 12 C
FIG. 12 D

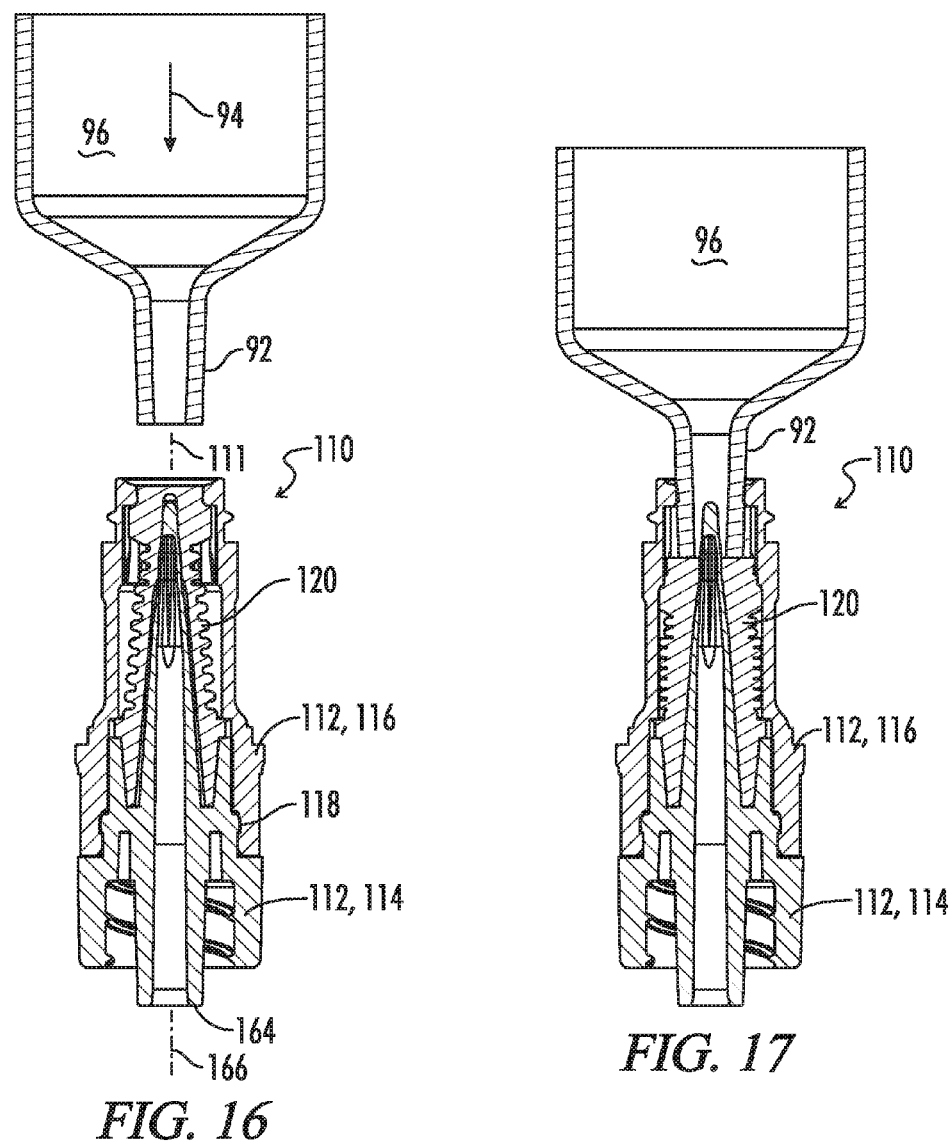

NEEDLELESS IV INJECTION PORT

TECHNICAL FIELD OF THE INVENTION

The present disclosure relates generally to medical intravenous administration line connectors. More particularly, this disclosure pertains to a needleless, intermittent, neutral fluid displacement injection ports for safe infusion of IV fluids, antibiotics, lipids, blood, blood components or drug products and/or blood aspiration in intravenous and blood administration therapy.

BACKGROUND OF THE INVENTION

In the mid-1980's, concern grew publically worldwide within the healthcare community for a new and potentially lethal virus called the Human Immunodeficiency Virus (HIV) which leads to AIDS (Acquired Immune Deficiency Syndrome). Prior to the AIDS epidemic, IV therapy and blood collection methods utilized hypodermic syringes and IV sets utilizing steel needles and latex injection ports to administer drugs and IV fluids along with blood collection samples. An accidental needle stick injury among healthcare providers was a common occurrence. Various viruses, fungi and bacterial infections (i.e. Hepatitis A, B, and C, *Staphylococcus, Tuberculosis*) could be transmitted to the healthcare provider via an accidental needle stick injury. Accidental punctures by contaminated needles can inject hazardous fluids into the body through the skin. There is potential for injection of hazardous drugs, but contact with infectious fluids, especially blood, is by far the greatest concern. Even small amounts of infectious fluid can spread certain diseases effectively through an accidental needle stick injury. The AIDS epidemic was the catalyst for change from high risk steel needles to needleless injection port devices for intermittent intravenous therapy and/or blood collection within the healthcare community.

Conventional "standalone" needleless injection ports include a body having a first portion that can be mated at one end to any patient's vascular access catheter, IV extension set, Huber needle set or IV bags and a second portion that can be mated to a standard syringe (without a steel hypodermic needle) or IV administration set (without a steel hypodermic needle) in order to infuse IV fluids, drugs, antibiotics, blood products or other fluids through the injection port and into the patient's bloodstream. Conventional standalone needleless injection ports can also have a second portion that can be mated to a blood collection device or syringe in order to aspirate blood samples from the patient. These conventional needleless injection ports can also be incorporated into an IV pump set or IV administration set in a Y-Injection Port configuration. Among the early and conventional needleless injection port internal fluid path designs introduced into the market since the early 1990's, many had the sole purpose to prevent accidental needlestick injuries for the healthcare provider.

Over the past 25 years, various conventional needleless injection ports have been introduced that utilize different functional design methods incorporating a two-way (infusion and aspiration capabilities), valve-type system for intermittent fluid delivery or aspiration. A combination of a resilient barrier(s) or seal(s) (i.e. silicone), steel springs, steel needles, steel blunt needles, and thermoplastic components have been utilized in conventional needleless injection ports.

The patient could receive antibiotics, normal saline/heparin, and other drugs or fluids through a standard syringe, or IV therapy through an IV administration set/IV bag. Blood samples are generally taken through a standard syringe or a blood collection device for chemical analysis. As the various fluid delivery medical devices are coupled to the injection port, the male-luer component of each of these fluid delivery medical devices will push down on the resilient barrier or seal to open the fluid pathway of the injection port in order to infuse fluids or draw blood samples through the injection port. Once the infusion or aspiration procedure is completed, the syringe, IV administration set, or blood collection device is removed from the injection port, the internal valve system reseals with the intent to prevent contamination from entering into the injection port fluid pathway system and potential catheter-related bloodstream infections (CR-BSIs).

Ever since needleless, intermittent injection ports were introduced to the markets in the early 1990's, two major patient safety issues have evolved; a significant increase in catheter-related bloodstream infections (CR-BSIs) and intraluminal thrombotic catheter occlusions (blood clots within the vascular-access catheter). Prior to needleless injection ports being introduced to the market in the early 1990's, CR-BSI's or intraluminal thrombotic catheter occlusions were not reported in medical journals when utilizing steel hypodermic needles and latex injection ports. It appears that needleless injection ports solved one major healthcare issue of eliminating accidental needlestick injuries, but, inadvertently created new patient safety issues.

Intravascular catheters play a central role in the care of critically and chronically ill patients; an estimated 7 million central venous catheters (CVCs) and peripherally-inserted central catheters (PICCs) and over 300 million peripheral IV catheters (PIV's) are inserted in patients each year in the United States alone as an integral part of today's patient care paradigm. These devices allow the administration of, among other things, parenteral nutrition, antibiotics, pain medication and large fluid volumes as well as provide access for blood sampling and blood component delivery. However, more than 250,000 catheter-related bloodstream infections (CR-BSI's) have been reported in medical journals to occur annually, with an estimated mortality rate of 12% to 25% (30,000 to 60,000 CR-BSI associated deaths every year in the United States). CR-BSI is not only one of the highest mortality infections in the hospital, but it also significantly increases hospital length of stay, with additional health care cost estimates of over $50,000 per occurrence (over $12 billion annually).

A second patient safety issue that has developed since the introduction of needleless injection ports is intraluminal thrombotic catheter occlusions, or blood clots within the vascular-access catheter. Catheter occlusion is defined as a partial or complete obstruction of the catheter lumen that limits or prevents the ability to withdraw blood, flush the catheter, and/or administer parenteral solutions or medications. Characterized by the inability to withdraw blood or infuse liquids, catheter occlusions occur in up to 25% of all CVCs and PICCs and are associated with interrupted intravascular therapy, often requiring either pharmacologic or even surgical approaches to restore catheter patency. Any of these events can negatively affect the patient's hospital experience. Discomfort associated with catheter restarts and IV site manipulation directly impacts the patient's perception of quality of care. Clinical complications associated with catheter occlusions can cost significant time and money and are also a critical factor in the overall patient care equation. It has been reported in the literature that typically 190 CVC/PICC catheters become occluded due to intraluminal thrombosis for every 1,500 catheters placed. Inability to access the patient's vascular system is not the only negative side effect of thrombus formation and catheter occlusion. Defined as a positive blood culture with clinical or microbiological evidence strongly implicating the catheter as the source of infection, catheter-related bloodstream infections (CR-BSIs) have been shown to have a strong correlation with the presence of catheter thrombi and fibrin sheaths in both animal and human studies. It is surmised that an intraluminal thrombosis may serve as a nidus for infections, perhaps due to the blood fibrin and biofilm depositions, thereby affecting the patient's health and increasing hospital costs.

Conventional needleless injection ports may also have other functional design deficiencies that could contribute to the increase in the two critical catheter care and maintenance issues facing healthcare today; catheter-related bloodstream infections (CR-BSIs) and intraluminal thrombotic catheter occlusions.

Poorly designed septum seal integrity, large gaps or openings at the critical outer septum area (or entry point), could allow microbial contamination ingress into the patient's injection port fluid pathway. Additionally, septum surface designs could make effective disinfection of the septum surface very difficult prior to accessing the needleless injection port; which could lead to downstream contamination into the patient's bloodstream. Most conventional needleless injection ports have torturous fluid pathways within their valve system designs that exhibit dead spaces that are difficult to effectively flush blood, air bubbles, and/or critical drugs from the injection port. Entrapped blood, within 24 hours, could begin developing blood fibrin and biofilm colonies within the injection port itself. The blood fibrin buildup within the injection port fluid pathway dead spaces can become a food source for microorganisms. Many conventional needleless injection ports with torturous fluid pathway valve designs have multiple-moving valve components within the fluid pathway of the injection port. This leads to large priming volumes (the amount of fluid to fill the fluid pathway of the needleless injection port), which increases the possibility for dead spaces within the injection port fluid pathway. Also, the majority of conventional needleless injection ports on the market exhibit either a negative or positive fluid displacement functional feature that exhibits a reflux of the patient's blood into the catheter lumen immediately upon disconnecting a syringe or IV set from the injection port (Negative Fluid Displacement designs) or reflux of the patient's blood immediately upon connecting a syringe or IV set to the injection port (Positive-Pressure Displacement designs). Most needleless injection ports are accessed many times over the life of the product; typically the life cycle for a conventional injection port is up to 72 to 96 hours before being replaced in an acute care hospital, and up to 7 days in a home care setting. This is due to a concern for potential infection and/or occlusion occurring. Each time blood is refluxed into the catheter lumen, blood fibrin develops on the inner wall of the catheter. The blood fibrin buildup contributes to intraluminal thrombotic catheter occlusions and becomes the food source for microorganisms coming down from the needleless injection port. The problems mentioned above can potentially be harmful to a patient or otherwise undesirably jeopardize the safety of the patient.

Additionally, the first and second portions of the injection port body in many conventional needleless injection ports are either sonically-welded or solvent-bonded together during the assembly process in manufacturing in order to firmly connect the two portions together and create an internal seal within the body. This manufacturing process can be difficult and time consuming, as well as costly.

What is needed, then, are improvements to a new needleless, intermittent injection port that is designed to reduce catheter-related bloodstream infections (CR-BSIs) and intraluminal thrombotic catheter occlusions, thereby, improving better patient safety and care.

BRIEF SUMMARY OF THE INVENTION

In one embodiment an injection port assembly includes a body having a first mating structure and a second mating structure configured to be coupled to the first mating structure. A resilient barrier is configured to be received within the body and is compressible from a less compressed first position in which fluid flow through the injection port assembly is blocked, to a more compressed second position in which fluid flow through the injection port assembly is permitted. The resilient barrier includes an internal cavity. When the resilient barrier is in a relaxed state, the internal cavity includes a cavity nose portion, a cavity sealing portion, and a cavity guide portion. The cavity nose portion has a cavity nose portion maximum inside diameter. The cavity sealing portion has a cavity sealing portion length, the cavity sealing portion having a cavity sealing portion inside diameter smaller than the cavity nose portion inside diameter along at least a majority of the cavity sealing portion length. The cavity guide portion is located on an opposite side of the cavity sealing portion from the cavity nose portion. The cavity guide portion has a cavity guide portion inside diameter greater than the cavity sealing portion inside diameter. A hollow cannula is coupled to the first mating structure and is configured to be received within the resilient barrier. The hollow cannula has a cannula distal end portion configured to extend through the resilient barrier when the resilient barrier is in the more compressed second position. The cannula distal end portion has at least one lateral outlet window having a window length less than the cavity sealing portion length. The cannula distal end portion includes a cannula nose located distally of the lateral outlet window and configured to be closely received in the cavity nose portion of the resilient barrier when the resilient barrier is in the less compressed first position. The cannula distal end portion both distally and proximally of the lateral outlet window has a cannula distal end portion outside diameter sufficiently greater than the cavity sealing portion inside diameter such that when the cannula is received in the resilient barrier with the cannula nose received in the cavity nose portion there is an interference fit between the cannula and the resilient barrier extending along the lateral outlet window and both proximally and distally of the lateral outlet window so that the cavity sealing portion of the resilient barrier seals across the lateral outlet window.

The cavity nose portion may be bulbous in shape and may have a semi-spherical distal end. The cavity nose portion may include a frusto-conical portion of increasing diameter in a proximal direction from the semi-spherical distal end to the cavity nose portion maximum inside diameter.

The cavity sealing portion may include a frusto-conical portion of increasing diameter in a proximal direction from a cavity sealing portion minimum inside diameter to a cavity sealing portion maximum inside diameter.

The cavity guide portion may include a frusto-conical portion of increasing diameter in a proximal direction from the cavity sealing portion.

The interference fit between the cannula and the resilient barrier may extend into the frusto-conical portion of the cavity guide portion.

The cavity guide portion may include a first frusto-conical portion of increasing diameter in a proximal direction adjacent the cavity sealing portion and a second frusto-conical portion adjacent the first frusto-conical portion, the second frusto-conical portion having a smaller included angle than the first frusto-conical portion.

The interference fit between the cannula and the resilient barrier may extend at least about 0.010 inch proximally and distally of the outlet window.

The cannula and the resilient barrier may be configured such that the interference fit provides at least about 0.001 inch radial interference between the cannula and the resilient barrier. Optionally the interference fit may provide at least about 0.002 inch radial interference. Optionally the interference fit may provide at least about 0.004 inch radial interference. Optionally the interference fit may provide at least about 0.006 inch radial interference.

The cannula nose may substantially fill the cavity nose portion when the resilient barrier is in the less compressed first position with the cannula nose closely received in the cavity nose portion.

When the resilient barrier is in a relaxed state the cavity sealing portion inside diameter may be smaller than the cavity nose portion maximum inside diameter along the entire cavity sealing portion length.

The at least one lateral outlet window in one embodiment includes two diametrically opposed outlet windows, and in another embodiment includes three circumferentially equally spaced outlet windows.

In another embodiment an injection port assembly includes a body having a first mating structure and a second mating structure configured to be coupled with the first mating structure. A resilient barrier may be received within the body and compressible between a less compressed first position in which fluid flow through the injection port assembly is blocked to a more compressed second position in which fluid flow through the injection port assembly is permitted. The resilient barrier includes an internal cavity. A hollow cannula is coupled to the first mating structure and configured to be received within the internal cavity of the resilient barrier. The hollow cannula may have a longitudinal central axis. The hollow cannula includes a cannula distal end portion configured to extend through the resilient barrier when the resilient barrier is in the more compressed second position. The cannula further includes at least one lateral outlet window formed in the cannula distal end portion, the at least one lateral outlet window having a window width perpendicular to the longitude central axis. An internal fluid passageway is defined in the hollow cannula and configured to communicate the at least one lateral outlet window with a fluid conduit connected to the first mating structure. The internal fluid passageway may have a non-circular cross section axially proximal from the window. The non-circular cross section may have a cross section area greater than a cross section area of a circle of diameter equal to the window width.

The at least one lateral outlet window may comprise two diametrically opposed outlet windows.

The two diametrically opposed outlet windows may be diametrically spaced apart by a window spacing.

The internal fluid passageway may extend laterally to each of the two diametrically opposed outlet windows and the non-circular cross section may have a first lateral cross section dimension at least equal to the window spacing immediately adjacent a proximal end of the windows.

The non-circular cross section immediately adjacent the proximal ends of the windows may have a second lateral cross section dimension perpendicular to the first lateral cross section dimension, which second lateral cross section dimension is at least equal to the window width.

The non-circular cross section of the internal fluid passageway may be at least partially defined between first and second generally parallel opposed interior walls of the hollow cannula.

The first and second interior walls may extend along a length of the windows.

The hollow cannula may further include first and second diametrically opposed reinforcing ribs extending radially inward from the first and second opposed interior walls, respectively, along at least the length of the windows.

The first and second reinforcing ribs may continue proximally beyond the length of the windows further into the internal fluid passageway.

The at least one lateral outlet window may comprise three circumferentially equally spaced outlet windows.

The non-circular cross section of the internal fluid passageway may be a three lobed cross section.

The three lobed cross section may taper radially outward and extend proximally from the windows for a distance at least as long as the window length.

The at least one window may have a window length, and the non-circular cross section of the internal fluid passageway may extend proximally beyond the length of the window further into the internal fluid passageway by a further distance at least as long as the window length.

In another embodiment the injection port assembly may include a snap lock feature for locking the first and second mating structures together. The snap lock feature may include a first locking portion and a second locking portion. One of the first and second locking portions may include a locking edge and the other of the first and second locking portions may include a tapered locking surface. The locking edge is configured to engage the tapered locking surface to resist disengagement of the first and second mating structures.

The locking edge may be defined by a substantially 90 degree corner.

The tapered locking surface may be a curved tapered locking surface.

The tapered locking surface may be defined on the second locking portion of the second mating structure, and the tapered locking surface may be a segmented surface defined on a plurality of stabilizing ring securement segments of the second mating structure.

The first and second locking portions may be configured such that a force of at least 30 pounds, and more preferably at least 40 pounds, is required to pull apart the first and second mating structures.

Numerous objects features and advantages of the present invention will be readily apparent to those skilled in the art upon a review of the following description when taken in conjunction with the accompanying drawings.

BRIEF DESCRIPTION OF THE DRAWINGS

FIG. 12 is an elevation view of a second embodiment of the lower body portion having three lateral outlet windows.

FIGS. 12A-12D are cross section views taken along lines 12A-12A, 12B-12B, 12C-12C and 12D-12D of FIG. 12.

FIG. 13 is an enlarged view of the distal end portion of the cannula of the lower body portion of FIG. 12.

FIG. 16 is an elevation cross section view of an injection port assembly using the lower body portion and resilient member of FIGS. 12 and 14 in the less compressed position of the resilient barrier. A syringe is shown in position about to be engaged with the injection port assembly.

FIG. 17 a view similar to FIG. 16, the syringe having been engaged with the injection port assembly to move the resilient barrier to its more compressed second position in which fluid flow through the injection port assembly is permitted.

DETAILED DESCRIPTION

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention.

The general arrangement of needleless IV injection ports and the various usages thereof in combination with other medical devices is described in greater detail in pending U.S. patent application Ser. No. 14/939,835 of Ryan entitled "Needleless, Intermittent, Neutral Displacement IV Injection Port" published as U.S. Patent Application Publication No. 2016/0129235, the details of which are incorporated herein by reference.

Embodiment of FIGS. 1-11

Figure 1:
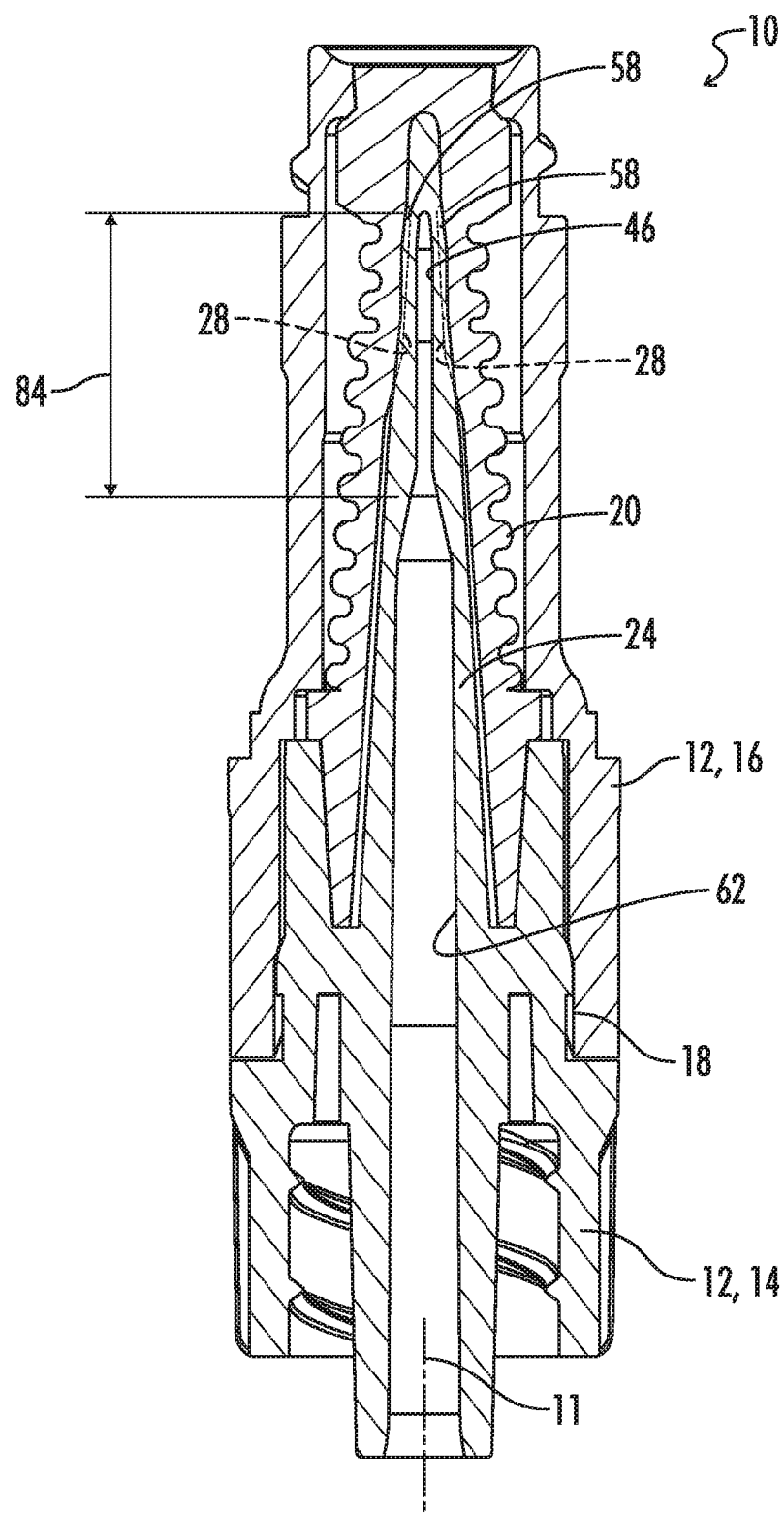
FIG. 1 is an elevation cross section view of an embodiment of the injection port assembly.
Figure 4:
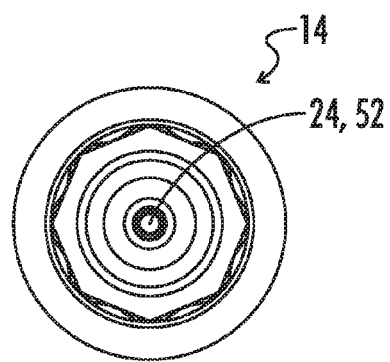
FIG. 4 is a top plan view of the first mating structure and cannula of FIG. 2.
Figure 2:
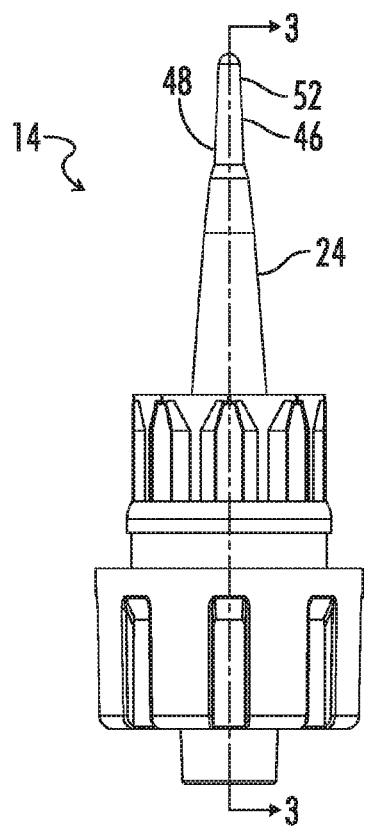
FIG. 2 is an elevation view of the first mating structure of the body, including the hollow cannula.

Referring now to the drawings, and particularly to FIG. 1, a first embodiment of an injection port assembly is shown and generally designated by the numeral 10. The injection port assembly 10 has a longitudinal axis 11. The injection port assembly 10 includes a body 12 made up of a first mating structure 14 and a second mating structure 16. The first mating structure 14 may also be referred to as a lower body part 14, and the second mating structure 16 may also be referred to as an upper body part 16. The first and second mating structures 14 and 16 are coupled together by a snap lock feature 18.

The injection port assembly 10 further includes a resilient barrier 20 which is configured to be received within the body 12 and which is compressible from a less compressed first position as seen for example in FIG. 1, in which fluid flow through the injection port assembly 10 is blocked, to a more compressed second position in which fluid flow through the injection port assembly 10 is permitted. It is noted that FIGS. 16 and 17 illustrate a similar less compressed first position and more compressed second position for the alternative embodiment of FIGS. 12-17, and FIGS. 16 and 17 are also representative of the change in shape of the resilient barrier 20 for the injection port assembly 10.

Figure 10:
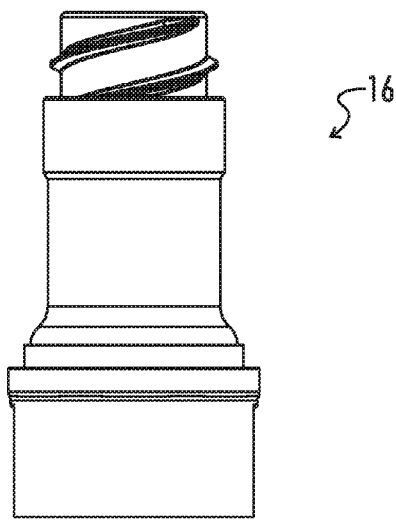
FIG. 10 is an elevation view of the second mating structure or upper body portion of the injection port assembly of FIG. 1.
Figure 11:
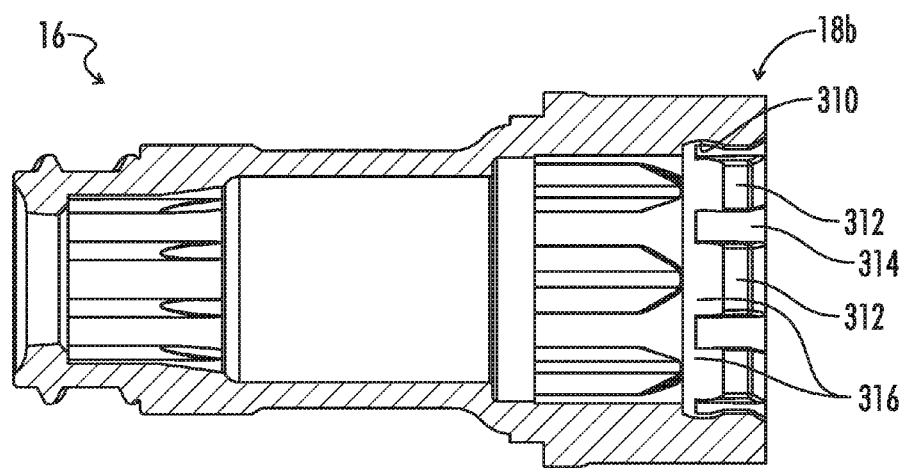
FIG. 11 is an elevation cross section view of the upper body portion of FIG. 10.

The details of construction of the first mating structure 14 are best shown in FIGS. 2-7. The details of construction of the second mating structure 16 are best shown in FIGS. 10 and 11. The details of construction of the resilient barrier 20 are best shown in FIGS. 8 and 9.

FIG. 1 shows the injection port assembly 10 in an assembled cross section view with the first and second mating structures 14 and 16 coupled together and with the resilient barrier 20 received within the body 12 between the first and second mating structures 14 and 16.

Figure 8:
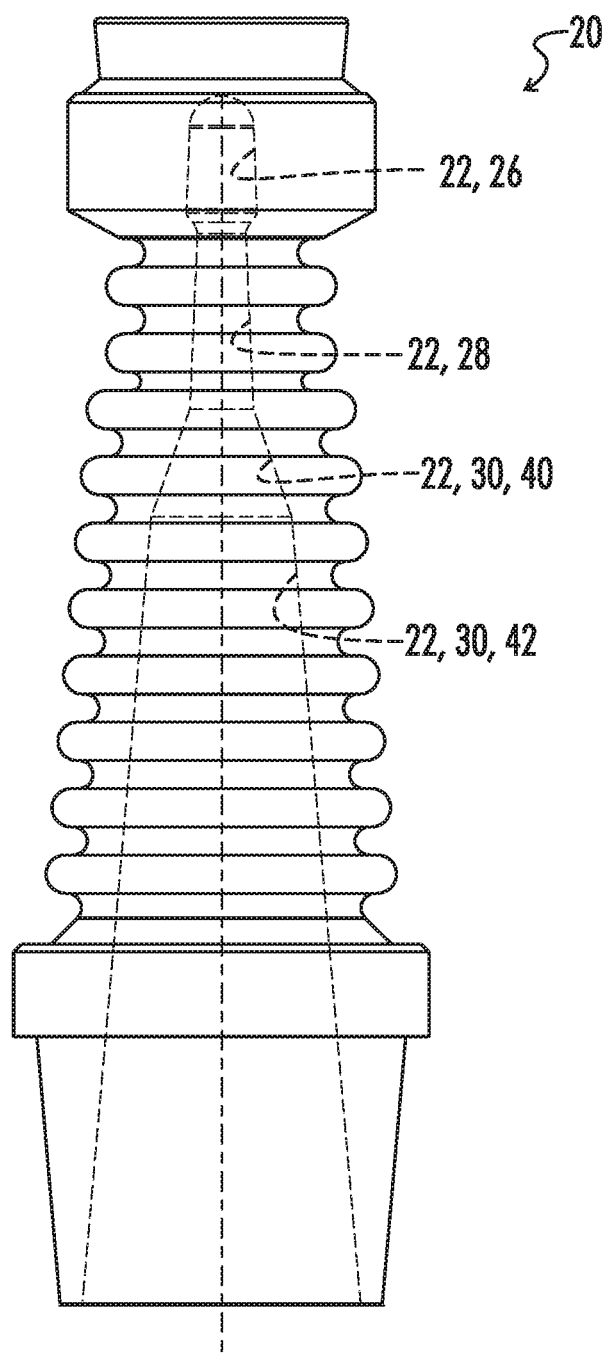
FIG. 8 is an elevation view of the resilient barrier of the injection port assembly of FIG. 1, with an internal cavity of the resilient barrier indicated in dashed lines.
Figure 9:
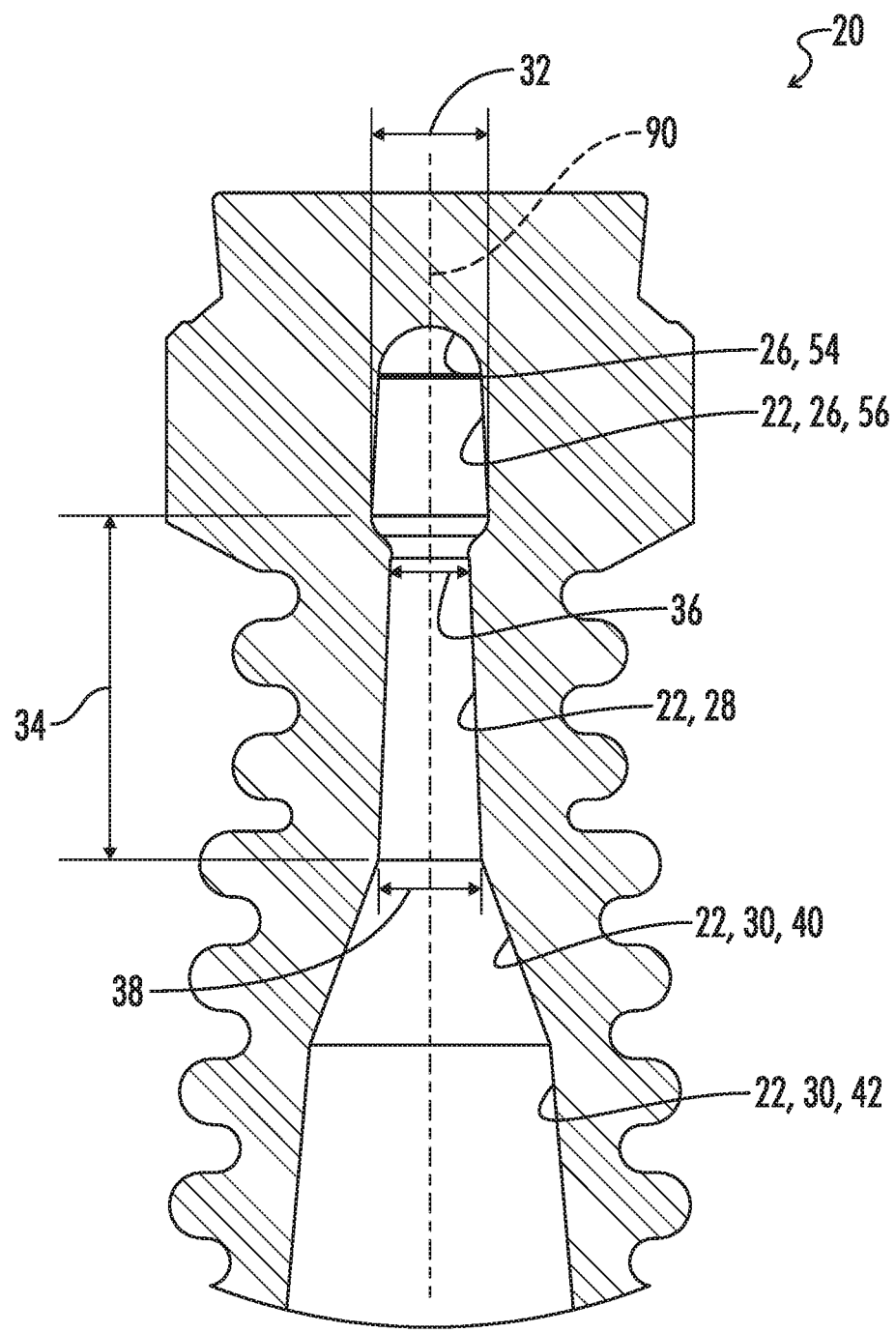
FIG. 9 is an enlarged elevation cross section view of the upper portion of the resilient barrier of FIG. 8.

As best seen in FIGS. 8 and 9, the resilient barrier 20 includes an internal cavity 22. It will be appreciated that the resilient barrier 20 is formed from an elastomeric material, and is shown in FIGS. 8 and 9 in its relaxed state in which the elastomeric material is relatively undeformed. It will also be appreciated that in FIG. 1 a hollow cannula 24 of the first mating structure 14 has been received in the internal cavity 22, thus deforming portions of the resilient barrier 20 radially outward so that the shape of the resilient barrier 20 as seen in FIG. 1, and particularly of its internal cavity 22, are different due to the resilient deformation thereof.

Referring now to FIGS. 8 and 9 which show the resilient barrier 20 and particularly its internal cavity 22 in their relaxed state, the internal cavity 22 in this relaxed state may be described as including a cavity nose portion 26, a cavity sealing portion 28, and a cavity guide portion 30.

As shown in FIG. 9, the cavity nose portion 26 has a cavity nose portion maximum inside diameter 32.

The cavity sealing portion 28 may be described as having a cavity sealing portion length 34. The cavity sealing portion 28 has a minimum cavity sealing portion inside diameter 36 at its upper end and is slightly tapered to a maximum cavity sealing portion inside diameter 38 at its lower end. It is noted that the cavity sealing portion 28 overall can be described as having a cavity sealing portion inside diameter smaller than the cavity nose portion maximum inside diameter 32 along at least a majority of the cavity sealing portion length 34. The cavity sealing portion inside diameter may be smaller than the cavity nose portion maximum inside diameter 32 along substantially the entire cavity sealing portion length 34.

The cavity sealing portion 28 of internal cavity 22 may be described as including a frusto-conical portion of increasing diameter in a proximal direction which increases from cavity sealing portion minimum inside diameter 36 to cavity sealing portion maximum inside diameter 38.

The cavity nose portion 26 may be described as being bulbous in shape as seen best in FIG. 9, and having a semi-spherical distal end 54. The cavity nose portion 26 may be further described as including a frusto-conical portion 56 of increasing diameter in a proximal direction from the semi-spherical distal end 54 to the cavity nose portion maximum inside diameter 32.

The cavity guide portion 30 is located on an opposite side of the cavity sealing portion 28 from the cavity nose portion 26. The cavity guide portion 30 tapers radially outward from the cavity sealing portion 28 and thus may be described as having a cavity guide portion inside diameter greater than the cavity sealing portion inside diameter 38. The cavity guide portion 30 may be further described as including a first frusto-conical portion 40 of increasing diameter in a proximal direction from the cavity sealing portion 38, and a second frusto-conical portion 42 adjacent the first frusto-conical portion 40, the second frusto-conical portion 42 having a smaller included angle than the first frusto-conical portion 40.

As previously noted, a hollow cannula 24 is coupled to the first mating structure 14, and in the example illustrated, the hollow cannula 24 is integrally formed with the first mating structure 14. The hollow cannula 24 is configured to be received within the resilient barrier 20 as shown for example in FIG. 1.

Figure 6:
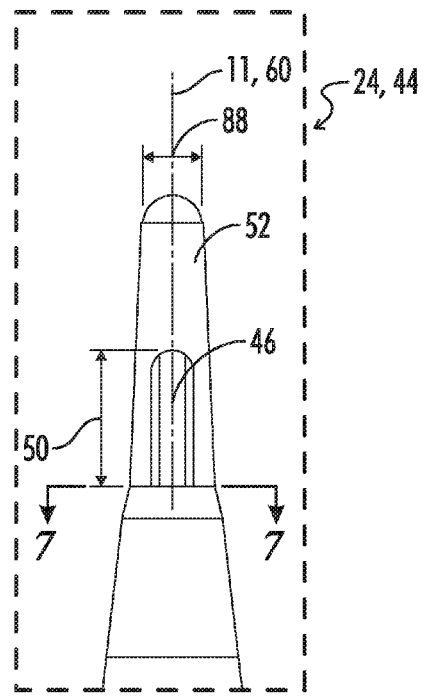
FIG. 6 is an enlarged view of the distal end portion of the cannula circled in FIG. 5.

The hollow cannula 24 includes a distal end portion 44 shown in enlarged view in FIG. 6. The distal end portion 44 is configured to extend through the resilient barrier 20 when the resilient barrier 20 is in the more compressed second position. The cannula distal end portion 44 has at least one lateral outlet window 46 and in the example shown has a pair of lateral outlet windows 46 and 48.

Figure 5:
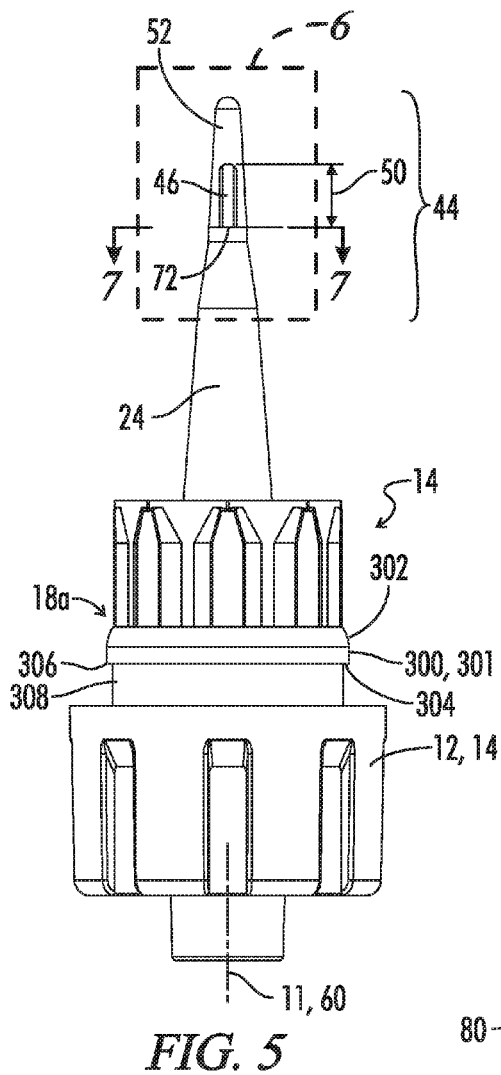
FIG. 5 is an elevation view of the first mating structure and cannula of FIG. 2, rotated 90° about the longitudinal axis as compared to FIG. 2.
Figure 7:
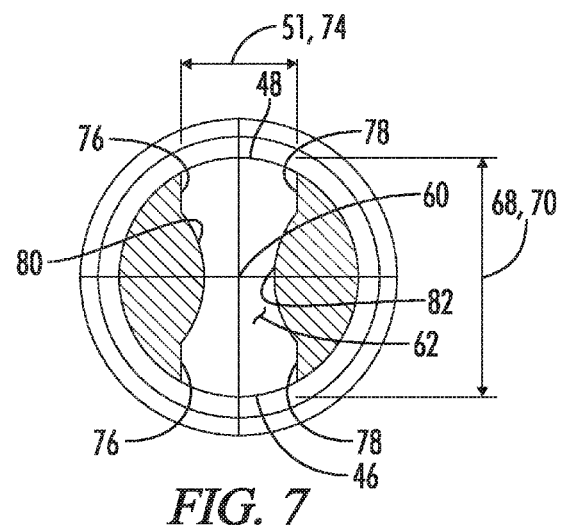
FIG. 7 is a cross section view taken along line 7-7 of FIG. 5 showing the non-circular cross section of the internal fluid passageway of the cannula.

As seen in FIGS. 5 and 6, each of the lateral outlet windows 46, 48 has a window length 50 which is less than the cavity sealing portion length 34. As best seen in FIG. 7, the windows 46 and 48 also have a width 51 perpendicular to the longitudinal central axis 11, 60 of the injection port assembly 10 and the cannula 24.

The cannula distal end portion 44 includes a cannula nose 52 located distally of the lateral outlet windows 46 and 48, and configured to be closely received in the cavity nose portion 26 of the resilient barrier 20 when the resilient barrier 20 is in the less compressed first position as shown in FIG. 1. The cannula nose may substantially fill the cavity nose portion when the resilient barrier is in the less compressed first position with the cannula nose closely received in the cavity nose portion. More particularly, the cannula nose may fill at least 90%, and more preferably at least 95%, of the cavity nose portion 96 by volume.

The cannula distal end portion 44 has a cannula distal end portion outside diameter both distally and proximally of the lateral outlet windows 46 and 48, which cannula distal end portion outside diameter is sufficiently greater than the respective inside diameters of the cavity sealing portion 28 of internal cavity 22 of resilient barrier 20 when the cannula nose 52 is received in the cannula nose portion 26 such that there is an interference fit between the cannula 24 and the resilient barrier 20. The interference fit extends along the lateral outlet windows 46 and 48 and both proximally and distally of the lateral outlet windows 46 and 48 so that the cavity sealing portion 28 of the resilient barrier 20 seals across the lateral outlet windows 46 and 48.

This is visualized in FIG. 1, wherein the relaxed position of the cavity sealing portion 28 of resilient barrier 20 is shown in dashed lines, and thus the extent of radially outward resilient deformation of the resilient barrier 20 by the cannula 24 received therein is readily apparent and it is apparent that this radially deformed portion of the cavity sealing portion 28 of resilient barrier 20 extends both distally and proximally from the lateral outlet windows 46 and 48.

The area between the dashed line relaxed state representation 28 and the solid line position of cavity sealing portion 28 as seen in FIG. 1 may be described as an interference fit 58 between the hollow cannula 24 and the resilient barrier 20. As is apparent in FIG. 1, this interference fit 58 between the cannula 24 and the resilient barrier 20 extends proximally into the first frusto-conical portion 40 of the cavity guide portion 30 of internal cavity 22 of resilient barrier 20. The interference fit 58 may also be described as a resilient interference zone spanning the length of the lateral windows 46 and 48.

At any one cross section along the axis 11 of injection port assembly 10, the interference fit 58 may be described as a radial interference which is mathematically determined by comparing the outside diameter of the cannula 24 to the inside diameter of the cavity sealing portion 28 in its relaxed state, and dividing that difference by two to provide the radial interference. Preferably the radial interference along the interference fit 58 is at least about 0.001 inch, optionally at least about 0.002 inch, optionally at least about 0.004 inch and optionally at least about 0.006 inch.

Preferably the interference fit 58 between the cannula 24 and the resilient barrier 20 extends at least about 0.010 inch both proximally and distally from the lateral outlet windows 46 and 48.

Non-Circular Cross Section Fluid Passageway

The hollow cannula 24 has a longitudinal central axis 60 which is coincident with the central axis 11 of the injection port assembly 10.

Figure 3:
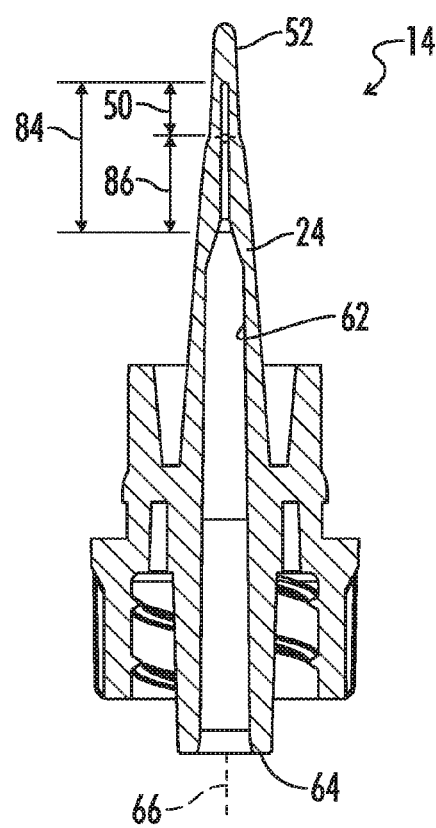
FIG. 3 is an elevation cross section view of the first mating structure and cannula taken along line 2-2 of FIG. 2.

The cannula 24 has an internal fluid passageway 62 defined therein as best seen in FIG. 3. The internal fluid passageway 62 communicates the lateral outlet windows 46 and 48 with a proximal end of the first mating structure 14 which is configured to communicate with a fluid conduit 66 schematically illustrated in FIG. 3. The fluid conduit 66 may be representative of any structure to which the injection port assembly 10 is to be connected for fluid flow therewith.

FIG. 7 shows a downward facing cross section of the cannula 24 taken along line 7-7 of FIG. 5 and shows that the internal fluid passageway 62 has a non-circular cross section axially proximal from the windows 46 and 48. This non-circular cross section may be described as having a cross sectional area greater than a cross section area of a circle of diameter equal to the window width 51.

The two outlet windows 46 and 48 may be described as being diametrically opposed as is best seen in FIG. 7, and as being diametrically spaced apart by a window spacing 68. The non-circular cross section internal fluid passageway 62 as seen in FIG. 7 may be described as extending laterally to each of the two diametrically opposed outlet windows 46 and 48, and the non-circular cross section has a first lateral cross section dimension 70 at least equal to the window spacing 68 at an axial location immediately adjacent to a proximal end 72 of the windows 46 and 48.

The non-circular cross section of the internal fluid passageway 62 as seen in FIG. 7 immediately adjacent the proximal ends 72 of windows 46 and 48 may also be described as having a second lateral cross section dimension 74 which is at least equal to the window width 51.

As is best visualized in FIG. 7, the non-circular cross section of the internal fluid passageway 62 may be described as being at least partially defined between first and second generally parallel opposed interior walls 76 and 78 of the hollow cannula 24.

The cannula 24 may further include first and second reinforcing ribs 80 and 82. The ribs 80 and 82 may be described as first and second diametrically opposed reinforcing ribs 80 and 82 extending radially inwardly from the first and second opposed interior walls 76 and 78, respectively.

This cross sectional shape of the internal fluid passageway 62 as visually depicted in FIG. 7 preferably extends along a non-circular cross section length 84 shown in FIG. 3. As is apparent in FIG. 3, the non-circular cross section length 84 extends along the window length 50 and continues proximally beyond the window length 50 into the internal passageway 62 of cannula 24 by a further distance 86 at least as long as the window length 50 and preferably longer than the window length 50.

Proximally of the non-circular cross sectional length 84, the internal passageway 62 may transition into a circular cross section extending to the proximal end 64 of the first mating structure 14.

The internal fluid passageway of non-circular cross section as depicted for example in FIG. 7 provides for increased fluid flow through the cannula 24 while maintaining the structural integrity of the cannula 24.

It will be appreciated by those skilled in the art that the typical dimensions of the cannula 24 are relatively small. For example, the cannula 24 may have an outside diameter 88 adjacent its distal end of approximately 0.04 inch, and the window width 51 may for example be approximately 0.026 inch. Thus if the internal fluid passageway 62 were of completely circular cross section as was typical in the prior art, a circular internal fluid passageway 62 leading to the lateral windows 46 and 48 would typically have a circular cross section with a diameter of about 0.026 inch. By constructing the cannula 24 with the non-circular cross sectional area depicted in FIG. 7 having a cross sectional area greater than a cross section of a circle of diameter equal to the window width 51, increased fluid flow through the cannula 24 for any given pressure of fluid supplied thereto is provided. Furthermore, due to the very small structures involved, the presence of the reinforcing ribs 80 and 82 aids in maintaining structural integrity of the tip portion of the cannula 24 around the windows 46 and 48, while still allowing this greater cross section internal passageway to be provided Improved Snap Lock Feature The snap lock feature 18 is improved over prior designs so as to provide a substantial increase in the tension force required to pull the first and second mating structures 14 and 16 apart after assembly.

Referring to FIG. 5, the first mating structure 14 includes a first locking portion 18a defined by a snap lock ring 300 having an outermost surface 301 defined between a tapered upper guiding surface 302 and a locking shoulder 304. The locking shoulder 304 is at substantially 90 degrees to the outer surface 301 thus defining a relatively sharp locking edge 306. Located below the snap lock ring 300 is a stabilizing ring shelf 308.

The second mating structure 16 includes a second locking portion 18b best seen in FIG. 11. The second locking portion 18b includes a snap lock ring channel 310 in which the snap lock ring 300 is to be received. Located below the snap lock ring channel 310 is a plurality of stabilizing ring securement segments 312 separated by gaps 314. It can be seen that the snap lock ring channel 310 is curved in cross-section and forms a curved tapered upper locking surface 316 on each of the stabilizing ring securement segments 312.

When the first and second mating structures 14 and 16 are snapped together as seen in FIG. 1. The sharp locking edge 306 of the snap lock ring 300 bites into the curved tapered upper locking surfaces 316 of the stabilizing ring securement segments 312 to securely prevent the first and second mating structures 14 and 16 from being pulled back apart.

When the current design is compared to a snap lock feature like that shown in U.S. Patent Application Publication No. 2016/0129235 wherein the engaging surfaces of the snap lock ring and of the stabilizing ring securement segments are both tapered at complementary angles, a substantial increase in the force required to pull apart the first and second mating structures is provided. The required pull apart force was increased from about 14 pounds with the design of U.S. Patent Application Publication No. 2016/0129235 to about 54 pounds with the present design. The snap lock feature 18 can be described as having the first and second locking portions 18a and 18b configured such that a force of at least 30 pounds, and more preferably at least 40 pounds, is required to pull apart the first and second mating structures 14 and 16.

Embodiment of FIGS. 12-17

An alternative embodiment of an injection port assembly having three lateral outlet windows instead of two lateral outlet windows is shown in FIGS. 12-17 and is generally designated by the number 110.

The injection port assembly 10 has a longitudinal axis 111. The injection port assembly 110 is shown in assembled cross section in FIG. 16 and includes a body 112 made up of a first mating structure 114 and a second mating structure 116. The first mating structure 114 may also be referred to as a lower body part 114, and the second mating structure 116 may also be referred to as an upper body part 116. The first and second mating structures 114 and 116 are coupled together by a snap lock feature 118.

The injection port assembly 110 further includes a resilient barrier 120 which is configured to be received within the body 112 and which is compressible from a less compressed first position as seen for example in FIG. 16, in which fluid flow through the injection port assembly 110 is blocked, to a more compressed second position as seen for example in FIG. 17, in which fluid flow through the injection port assembly 110 is permitted.

The details of construction of the first mating structure 114 are best shown in FIGS. 12-13. The details of construction of the second mating structure 116 are substantially the same as was shown for the second mating structure 16 in FIGS. 10 and 11. The details of construction of the resilient barrier 120 are best shown in FIGS. 14 and 15.

FIG. 16 shows the injection port assembly 110 in an assembled cross section view with the first and second mating structures 114 and 116 coupled together and with the resilient barrier 120 received within the body 112 between the first and second mating structures 114 and 116.

Figure 14:
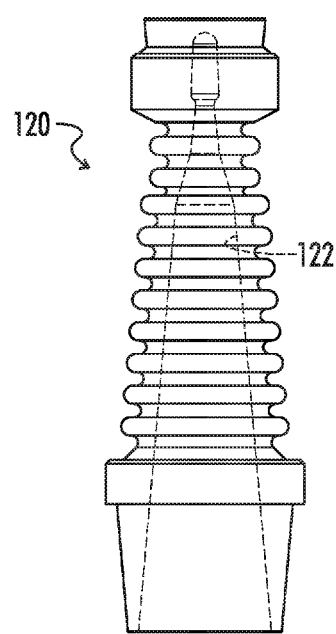
FIG. 14 is an elevation view of a second embodiment of the resilient barrier, for use with the lower body portion of FIG. 12.
Figure 15:
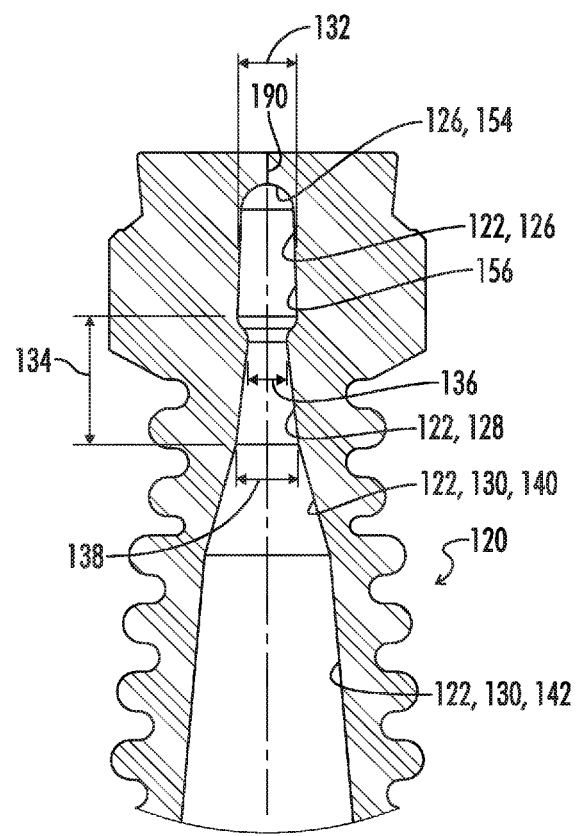
FIG. 15 is an enlarged cross section view of the distal end portion of the resilient barrier of FIG. 14.

As best seen in FIGS. 14 and 15, the resilient barrier 120 includes an internal cavity 122. It will be appreciated that the resilient barrier 120 is formed from an elastomeric material, and is shown in FIGS. 14 and 15 in its relaxed state in which the elastomeric material is relatively undeformed. It will also be appreciated that in FIG. 16 a hollow cannula 124 of the first mating structure 114 has been received in the internal cavity 122, thus deforming portions of the resilient barrier 120 radially outward so that the shape of the resilient barrier 120 as seen in FIG. 16, and particularly of its internal cavity 122, are different due to the resilient deformation thereof.

Referring now to FIGS. 14 and 15 which show the resilient barrier 120 and particularly its internal cavity 122 in their relaxed state, the internal cavity 122 in this relaxed state may be described as including a cavity nose portion 126, a cavity sealing portion 128, and a cavity guide portion 130.

As shown in FIG. 15, the cavity nose portion 126 has a cavity nose portion maximum inside diameter 132.

The cavity sealing portion 128 may be described as having a cavity sealing portion length 134. The cavity sealing portion 128 has a minimum cavity sealing portion inside diameter 136 at its upper end and is slightly tapered to a maximum cavity sealing portion inside diameter 138 at its lower end. It is noted that the cavity sealing portion 128 overall can be described as having a cavity sealing portion inside diameter smaller than the cavity nose portion maximum inside diameter 132 along at least a majority of the cavity sealing portion length 134. The cavity sealing portion inside diameter may be smaller than the cavity nose portion maximum inside diameter 132 along substantially the entire cavity sealing portion length 34.

The cavity sealing portion 128 of internal cavity 122 may be described as including a frusto-conical portion of increasing diameter in a proximal direction which increases from cavity sealing portion minimum inside diameter 136 to cavity sealing portion maximum inside diameter 138.

The cavity nose portion 126 may be described as being bulbous in shape as seen best in FIG. 15, and having a semi-spherical distal end 154. The cavity nose portion 126 may be further described as including a frusto-conical portion 156 of increasing diameter in a proximal direction from the semi-spherical distal end 154 to the cavity nose portion maximum inside diameter 132.

The cavity guide portion 130 is located on an opposite side of the cavity sealing portion 128 from the cavity nose portion 126. The cavity guide portion 130 tapers radially outward from the cavity sealing portion 128 and thus may be described as having a cavity guide portion inside diameter greater than the cavity sealing portion inside diameter 138. The cavity guide portion 130 may be further described as including a first frusto-conical portion 140 of increasing diameter in a proximal direction from the cavity sealing portion 138, and a second frusto-conical portion 142 adjacent the first frusto-conical portion 140, the second frusto-conical portion 142 having a smaller included angle than the first frusto-conical portion 140.

As previously noted, a hollow cannula 124 is coupled to the first mating structure 114, and in the example illustrated, the hollow cannula 124 is integrally formed with the first mating structure 114. The hollow cannula 124 is configured to be received within the resilient barrier 120 as shown for example in FIG. 16.

The hollow cannula 124 includes a distal end portion 144 shown in enlarged view in FIG. 13. The distal end portion 144 is configured to extend through the resilient barrier 120 when the resilient barrier 120 is in the more compressed second position of FIG. 17. The cannula distal end portion 144 has at least one lateral outlet window 146 and in the example shown has three lateral outlet windows 146, 147 and 148.

As seen in FIGS. 12 and 13, each of the lateral outlet windows 146, 147 and 148 has a window length 150 which is less than the cavity sealing portion length 134. As best seen in FIG. 12C, the windows 146, 147 and 148 also have a width 151 perpendicular to the longitudinal central axis 111, 160 of the injection port assembly 110 and the cannula 124.

The cannula distal end portion 144 includes a cannula nose 152 located distally of the lateral outlet windows 146, 147 and 148, and configured to be closely received in the cavity nose portion 126 of the resilient barrier 120 when the resilient barrier 120 is in the less compressed first position as shown in FIG. 16.

The cannula distal end portion 144 has a cannula distal end portion outside diameter both distally and proximally of the lateral outlet windows 146, 147 and 148, which cannula distal end portion outside diameter is sufficiently greater than the respective inside diameters of the cavity sealing portion 128 of internal cavity 122 of resilient barrier 120 when the cannula nose 152 is received in the cannula nose portion 126 such that there is an interference fit between the cannula 124 and the resilient barrier 120. The interference fit extends along the lateral outlet windows 146, 147 and 148 and both proximally and distally of the lateral outlet windows 146, 147 and 148 so that the cavity sealing portion 128 of the resilient barrier 120 seals across the lateral outlet windows 146, 147 and 148.

Preferably the radial interference along the interference fit is at least about 0.001 inch, optionally at least about 0.002 inch, optionally at least about 0.004 inch and optionally at least about 0.006 inch. Preferably the interference fit between the cannula 124 and the resilient barrier 120 extends at least about 0.010 inch both proximally and distally from the lateral outlet windows 146, 147 and 148.

The hollow cannula 124 has a longitudinal central axis 160 which is coincident with the central axis 111 of the injection port assembly 110.

The cannula 124 has an internal fluid passageway 162 defined therein as best seen in FIGS. 12A-12C. The internal fluid passageway 162 communicates the lateral outlet windows 146, 147 and 148 with a proximal end of the first mating structure 114 which is configured to communicate with a fluid conduit 166 schematically illustrated in FIG. 16. The fluid conduit 166 may be representative of any structure to which the injection port assembly 110 is to be connected for fluid flow therewith.

FIG. 12D shows an upward facing cross section of the cannula 124 taken along line D-D of FIG. 12. FIGS. 12A, 12B and 12C show downward facing cross sections of the cannula 124 taken along lines A-A, B-B and C-C, respectively. FIGS. 12A-12C show that the internal fluid passageway 162 has a non-circular cross section axially proximal from the windows 146, 147 and 148. This non-circular cross section may be described as having a cross sectional area greater than a cross section area of a circle of diameter equal to the window width 151.

The three outlet windows 146, 147 and 148 may be described as being equally circumferentially spaced about the axis 160. The non-circular cross section internal fluid passageway 162 as seen in FIGS. 12A-12D may be described as extending laterally to each of the outlet windows 146, 147 and 148.

The non-circular cross section of internal fluid passageway 162 may be described as a three lobed cross section. As can be seen in comparing FIGS. 12A, 12B and 12C, the three lobed cross section tapers radially outward. This cross sectional shape of the internal fluid passageway 62 as visually depicted in FIGS. 12A-12C preferably extends along a non-circular cross section length 184 shown in FIG. 13. As is apparent in FIG. 13, the non-circular cross section length 184 extends along the window length 150 and continues proximally beyond the window length 150 into the internal passageway 162 of cannula 124 by a further distance 186 at least as long as the window length 150 and preferably longer than the window length 150. Proximally of the non-circular cross sectional length 184, the internal passageway 162 may transition into a circular cross section extending to the proximal end 164 of the first mating structure 114.

Improved Performance

The provision of the interference fit 58 between the cannula 24 and the resilient barrier 20 of FIGS. 1-11, and of the cannula 124 and resilient barrier 120 of the embodiment of FIGS. 12-17, has provided substantially increased resistance to leaking due to back pressure within the injection port assemblies 10 and 110 as compared to a similar prior design of the assignee of the present invention as depicted in U.S. Patent Application Publication No. 2016/0129235.

For example, using the embodiment of FIGS. 12-17, tests were run on back pressure resistance, flow rate and fluid displacement.

Average back pressure resistance has improved from 47 psi with the previous design to over 68 psi with the design depicted herein having the interference fit. Testing was done using standardized procedures wherein each sample was submerged in water and subjected to increased pressure until air bubbles were observed leaking from the submerged sample.

Average fluid flow rates at gravity increased from 48 mL/min for a similar design having a circular cross section internal fluid passageway, up to an average of approximately 139 mL/min for the cross sectional area generally like that shown in FIG. 12A-12C. In these tests for a lot of 59 samples, flow rates ranged from a minimum of 127 mL/min to a max of 155 mL/min for sterilized samples, and from a minimum of 127 mL/min to a max of 163 mL/min for non-sterilized samples Additionally, fluid reflux was measured at 0.00 mL with the embodiment of FIGS. 12-17.

Methods of Use

As depicted in FIGS. 1 and 16 for the respective embodiments, the upper and lower parts 16, 116 and 14, 114 of the bodies 12, 112 are assembled with the resilient barriers 20, 120 contained therein and with the cannula 24, 124 received with the internal cavity 22, 122 of respective resilient barrier 20, 120. It will be appreciated that in the assembled arrangement as seen in FIGS. 1 and 16, there may be a slight axial compression of the resilient barrier 20, 120 from its completely relaxed state. The position of the resilient barrier 20, 120 as depicted in FIGS. 1 and 16 may be described as a less axially compressed first position in which fluid flow through the injection port assembly 10, 110 is blocked. It will be appreciated that the distal end of the resilient barrier 20, 120 has a precut slit 90, 190 formed therein through which the distal end portion 44, 144 of cannula 24, 124 will protrude when the resilient barrier 20, 120 is moved to its more axially compressed second position like that shown in FIG. 17.

Figure 18:
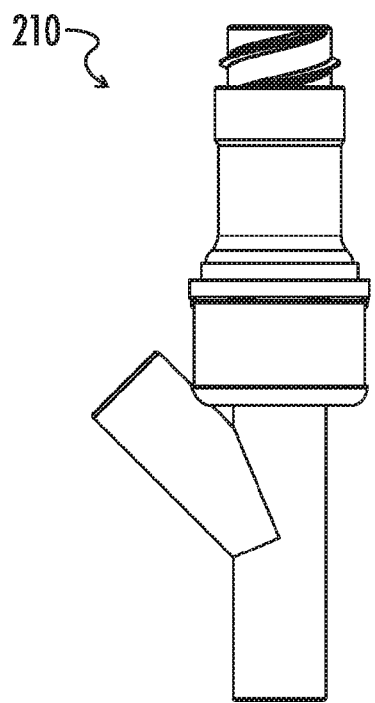
FIG. 18 is an elevation view of a Y-site injection port assembly including the resilient member and cannula construction of FIGS. 12-17.
Figure 19:
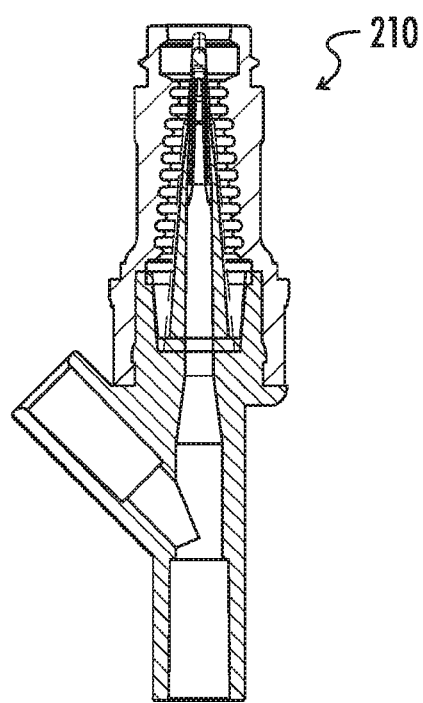
FIG. 19 is an elevation cross section view of the Y-site injection port assembly of FIG. 18.

The injection port assembly 10, 110 may be connected to various conduits and medical devices so as to provide for intravenous injection into the patient's body and for collection of blood samples from the patient. The injection port assembly 10 may be incorporated into an IV pump set or IV administration set in a Y-site injection port configuration. FIGS. 18 and 19 for example, show a Y-site injection port arrangement 210 utilizing the three window embodiment of FIGS. 12-17.

As depicted in FIGS. 16 and 17, the resilient barrier 120 may be moved from its closed first position to its open second position by engagement of the injection port assembly 110 by a male-luer slip syringe 92. Beginning in the closed position of FIG. 16, as is indicated by the arrow 94 the syringe 92 is pushed downward engaging the distal end of the resilient barrier 120 and forcing it downward relative to the cannula 124 so as to expose the distal end portion 144 of cannula 124 thus allowing the lateral windows such as 146, 147 and 148 to communicate with the interior 96 of syringe 92. This allows fluids to be injected into or withdrawn from the patient's blood stream.

The resilient barrier 20, 120 may for example be formed of a silicone rubber material having a diameter in the range of from about 50 to about 70, and preferably having a diameter of about 60. The silicone rubber material may have a small amount of phenyl oil included therein to provide an internal lubricant when the resilient barrier 20, 120 slides along the outer surface of the cannula 24, 124. The exterior surface of cannula 24, 124 may be treated to form a slightly roughened surface with irregularities on the order of 0.001 inch and may be lubricated with silicone oil to further aid in the movement of the resilient barrier 20 between its closed and open positions of FIGS. 16 and 17. These features aid in allowing the resilient barrier 20, 120 to substantially instantaneously snap back from its open position of FIG. 17 to its closed position of FIG. 16 upon removal of the syringe 92.

Thus it is seen that the apparatus and methods of the present invention readily achieve the ends and advantages mentioned as well as those inherent therein. While certain preferred embodiments have been illustrated and described for purposes of the present disclosure, numerous changes in the arrangement and construction of parts and steps will be apparent to those skilled in the art, which changes are encompassed within the scope and spirit of the present invention as defined by the appended claims.

What is claimed is:

1. An injection port assembly, comprising:
   a body having a first mating structure and a second mating structure configured to be coupled to the first mating structure;
   a resilient barrier configured to be received within the body and compressible from a less compressed first position in which fluid flow through the injection port assembly is blocked to a more compressed second position in which fluid flow through the injection port assembly is permitted, the resilient barrier including an internal cavity, the internal cavity when the resilient barrier is in a relaxed state including:
      a cavity nose portion having a cavity nose portion maximum inside diameter;
      a cavity sealing portion having a cavity sealing portion length, the cavity sealing portion having a cavity sealing portion inside diameter smaller than the cavity nose portion maximum inside diameter along at least a majority of the cavity sealing portion length; and
      a cavity guide portion located on an opposite side of the cavity sealing portion from the cavity nose portion, the cavity guide portion having a cavity guide portion inside diameter greater than the cavity sealing portion inside diameter; and
   a hollow cannula coupled to the first mating structure and configured to be received within the resilient barrier, the hollow cannula having a cannula distal end portion configured to extend through the resilient barrier when the resilient barrier is in the more compressed second position, the cannula distal end portion having at least one lateral outlet window having a window length less than the cavity sealing portion length, the cannula distal end portion including a cannula nose located distally of the lateral outlet window and configured to be closely received in the cavity nose portion of the resilient barrier when the resilient barrier is in the less compressed first position, the cannula distal end portion both distally and proximally of the lateral outlet window having a cannula distal end portion outside diameter sufficiently greater than the cavity sealing portion inside diameter such that when the cannula is received in the resilient barrier with the cannula nose received in the cavity nose portion there is an interference fit between the cannula and the resilient barrier extending along the lateral outlet window and both proximally and distally of the lateral outlet window so that the cavity sealing portion of the resilient barrier seals across the lateral outlet window;

wherein the cavity nose portion is bulbous in shape and has a semi-spherical distal end, and the cavity nose portion includes a frusto-conical portion of increasing diameter in a proximal direction from the semi-spherical distal end to the cavity nose portion maximum inside diameter.

2. The injection port assembly of claim 1, wherein:
the cavity sealing portion includes a frusto-conical portion of increasing diameter in a proximal direction from a cavity sealing portion minimum inside diameter to a cavity sealing portion maximum inside diameter.

3. The injection port assembly of claim 1, wherein:
the cavity guide portion includes a frusto-conical portion of increasing diameter in a proximal direction from the cavity sealing portion.

4. The injection port assembly of claim 3, wherein:
the interference fit between the cannula and the resilient barrier extends into the frusto-conical portion of the cavity guide portion.

5. The injection port assembly of claim 1, wherein:
the cavity guide portion includes a first frusto-conical portion of increasing diameter in a proximal direction adjacent the cavity sealing portion and a second frusto-conical portion adjacent the first frusto-conical portion, the second frusto-conical portion having a smaller included angle than the first frusto-conical portion.

6. The injection port assembly of claim 1, wherein:
the interference fit between the cannula and the resilient barrier extends at least about 0.010 inch proximally and distally of the outlet window.

7. The injection port assembly of claim 1, wherein:
the cannula and the resilient barrier are configured such that interference fit provides at least about 0.001 inch radial interference between the cannula and the resilient barrier.

8. The injection port assembly of claim 1, wherein:
the cannula and the resilient barrier are configured such that interference fit provides at least about 0.002 inch radial interference between the cannula and the resilient barrier.

9. The injection port assembly of claim 1, wherein:
the cannula and the resilient barrier are configured such that interference fit provides at least about 0.004 inch radial interference between the cannula and the resilient barrier.

10. The injection port assembly of claim 1, wherein:
the cannula nose substantially fills the cavity nose portion when the resilient barrier is in the less compressed first position with the cannula nose closely received in the cavity nose portion.

11. The injection port assembly of claim 1, wherein:
when the resilient barrier is in the relaxed state the cavity sealing portion inside diameter is smaller than the cavity nose portion maximum inside diameter along the entire cavity sealing portion length.

12. The injection port assembly of claim 1, wherein:
the at least one lateral outlet window comprises two diametrically opposed outlet windows.

13. The injection port assembly of claim 1, wherein:
the at least one lateral outlet window comprises three circumferentially equally spaced outlet windows.

14. An injection port assembly, comprising:
a body having a first mating structure and a second mating structure configured to be coupled to the first mating structure;
a resilient barrier configured to be received within the body and compressible from a less compressed first position in which fluid flow through the injection port assembly is blocked to a more compressed second position in which fluid flow through the injection port assembly is permitted, the resilient barrier including an internal cavity, the internal cavity when the resilient barrier is in a relaxed state including:
a cavity nose portion having a cavity nose portion maximum inside diameter;
a cavity sealing portion having a cavity sealing portion length, the cavity sealing portion having a cavity sealing portion inside diameter smaller than the cavity nose portion maximum inside diameter along at least a majority of the cavity sealing portion length; and
a cavity guide portion located on an opposite side of the cavity sealing portion from the cavity nose portion, the cavity guide portion having a cavity guide portion inside diameter greater than the cavity sealing portion inside diameter; and
a hollow cannula coupled to the first mating structure and configured to be received within the resilient barrier, the hollow cannula having a cannula distal end portion configured to extend through the resilient barrier when the resilient barrier is in the more compressed second position, the cannula distal end portion having at least one lateral outlet window having a window length less than the cavity sealing portion length, the cannula distal end portion including a cannula nose located distally of the lateral outlet window and configured to be closely received in the cavity nose portion of the resilient barrier when the resilient barrier is in the less compressed first position, the cannula distal end portion both distally and proximally of the lateral outlet window having a cannula distal end portion outside diameter sufficiently greater than the cavity sealing portion inside diameter such that when the cannula is received in the resilient barrier with the cannula nose received in the cavity nose portion there is an interference fit between the cannula and the resilient barrier extending along the lateral outlet window and both proximally and distally of the lateral outlet window so that the cavity sealing portion of the resilient barrier seals across the lateral outlet window;

wherein the cannula nose substantially fills the cavity nose portion when the resilient barrier is in the less compressed first position with the cannula nose closely received in the cavity nose portion.

15. The injection port assembly of claim 14, wherein:
the cavity sealing portion includes a frusto-conical portion of increasing diameter in a proximal direction from a cavity sealing portion minimum inside diameter to a cavity sealing portion maximum inside diameter.

16. The injection port assembly of claim 14, wherein:
the cavity guide portion includes a frusto-conical portion of increasing diameter in a proximal direction from the cavity sealing portion.

17. The injection port assembly of claim 16, wherein:
the interference fit between the cannula and the resilient barrier extends into the frusto-conical portion of the cavity guide portion.

18. The injection port assembly of claim 14, wherein:
the cavity guide portion includes a first frusto-conical portion of increasing diameter in a proximal direction adjacent the cavity sealing portion and a second frusto-conical portion adjacent the first frusto-conical portion, the second frusto-conical portion having a smaller included angle than the first frusto-conical portion.

19. The injection port assembly of claim 14, wherein:
the interference fit between the cannula and the resilient barrier extends at least about 0.010 inch proximally and distally of the outlet window.

20. The injection port assembly of claim 14, wherein:
the cannula and the resilient barrier are configured such that interference fit provides at least about 0.001 inch radial interference between the cannula and the resilient barrier.

21. The injection port assembly of claim 14, wherein:
the cannula and the resilient barrier are configured such that interference fit provides at least about 0.002 inch radial interference between the cannula and the resilient barrier.

22. The injection port assembly of claim 14, wherein:
the cannula and the resilient barrier are configured such that interference fit provides at least about 0.004 inch radial interference between the cannula and the resilient barrier.

23. The injection port assembly of claim 14, wherein:
when the resilient barrier is in the relaxed state the cavity sealing portion inside diameter is smaller than the cavity nose portion maximum inside diameter along the entire cavity sealing portion length.

24. The injection port assembly of claim 14, wherein:
the at least one lateral outlet window comprises two diametrically opposed outlet windows.

25. The injection port assembly of claim 14, wherein:
the at least one lateral outlet window comprises three circumferentially equally spaced outlet windows.

* * * * *